(12) United States Patent
Bryant et al.

(10) Patent No.: US 9,333,124 B2
(45) Date of Patent: May 10, 2016

(54) ABSORBENT ARTICLE HAVING ASYMMETRIC PRINTED PATTERNS FOR PROVIDING A FUNCTIONAL CUE

(75) Inventors: Kristi Bryant, Greenville, WI (US); Sue Oates, Appleton, WI (US); Garry Woltman, Appleton, WI (US); HyungByum Kim, GyeongGi-do (KR); Julie Prescher, Larsen, WI (US); Ward Elwood, Kalamazoo, MI (US); Shelley Rasmussen, Sr., Oshkosh, WI (US); Dave Krysiak, Menasha, WI (US); HyungWoo Park, GyeongGi-do (KR); Clarice Theisen, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 141 days.

(21) Appl. No.: 13/990,140

(22) PCT Filed: Nov. 30, 2010

(86) PCT No.: PCT/US2010/058347
§ 371 (c)(1),
(2), (4) Date: Aug. 6, 2013

(87) PCT Pub. No.: WO2012/074512
PCT Pub. Date: Jun. 7, 2012

(65) Prior Publication Data
US 2013/0310784 A1 Nov. 21, 2013

(51) Int. Cl.
*A61F 13/15* (2006.01)
*A61F 13/20* (2006.01)
(Continued)

(52) U.S. Cl.
CPC ..... *A61F 13/51394* (2013.01); *A61F 13/51496* (2013.01); *A61L 15/56* (2013.01)

(58) Field of Classification Search
CPC ............... A61F 13/51394; A61F 13/51496; A61F 2013/8497
USPC .............................. 604/367, 378, 385.01, 361
See application file for complete search history.

(56) References Cited

U.S. PATENT DOCUMENTS 4,022,211 A 5/1977 Timmons et al.
4,292,916 A 10/1981 Bradley et al.
(Continued)

FOREIGN PATENT DOCUMENTS

CN 201320256 10/2009
EP 1 306 069 A2 5/2003
(Continued)

OTHER PUBLICATIONS

Abstract of European Patent—EP 0 554 565, Aug. 11, 1993, 2 pages.
(Continued)

*Primary Examiner* — Michele M Kidwell
(74) *Attorney, Agent, or Firm* — Dority & Manning, P.A.

(57) ABSTRACT

A feminine care absorbent article that contains multiple printed patterns of graphical objects visible from a body facing surface is provided. The layout and design of the patterns are carefully selected in the present invention to achieve a synergistic masking effect that helps visually disguise the presence of bodily fluids or stains around the periphery of the article. Such "passive" stain masking is achieved, in part, through the use of printed patterns that are distributed in an asymmetric manner about both the longitudinal and transverse centerlines of the article. The printed patterns are also located at or near the periphery of the article and at least partially extend into portions of the body facing surface that overlie the absorbent core. The pattern design is also such that a majority of an interior zone of the absorbent article is generally free of printed graphical objects.

17 Claims, 6 Drawing Sheets

(51) Int. Cl.
*A61F 13/513* (2006.01)
*A61F 13/514* (2006.01)
*A61L 15/56* (2006.01)

(56) References Cited

U.S. PATENT DOCUMENTS

| | | | |
|---|---|---|---|
| 4,798,603 | A | 1/1989 | Meyer et al. |
| 4,801,494 | A | 1/1989 | Datta et al. |
| 4,812,053 | A | 3/1989 | Bhattacharjee |
| 4,892,534 | A | 1/1990 | Datta et al. |
| 4,903,254 | A | 2/1990 | Haas |
| 4,908,026 | A | 3/1990 | Sukiennik et al. |
| 4,987,849 | A | 1/1991 | Sherman |
| 5,045,283 | A | 9/1991 | Patel |
| 5,053,339 | A | 10/1991 | Patel |
| 5,058,088 | A | 10/1991 | Haas et al. |
| 5,248,309 | A | 9/1993 | Serbiak et al. |
| 5,417,748 | A | 5/1995 | Kawashima |
| 5,614,295 | A | 3/1997 | Quincy, III et al. |
| 5,912,194 | A | 6/1999 | Everhart et al. |
| 5,993,940 | A | 11/1999 | Ouderkirk et al. |
| 5,993,949 | A | 11/1999 | Rosenbaum et al. |
| 6,297,424 | B1 | 10/2001 | Olson et al. |
| 6,307,110 | B1 | 10/2001 | Argyropoulos et al. |
| 6,307,119 | B1 | 10/2001 | Cammarota et al. |
| 6,350,711 | B1 | 2/2002 | Potts et al. |
| D476,416 | S | 6/2003 | MacDonagh |
| 6,635,797 | B2 | 10/2003 | Olson et al. |
| D483,479 | S | 12/2003 | Braverman et al. |
| 7,107,621 | B2 | 9/2006 | Meekins |
| 7,258,684 | B2 | 8/2007 | Bryant et al. |
| D552,236 | S | 10/2007 | Fernandez Picon |
| 7,322,472 | B2 | 1/2008 | Swiecicki et al. |
| 7,402,157 | B2 | 7/2008 | Christon et al. |
| D594,972 | S | 6/2009 | Cauwood et al. |
| D600,797 | S | 9/2009 | Nelson et al. |
| D601,696 | S | 10/2009 | Nelson et al. |
| 7,626,072 | B2 | 12/2009 | Mocadlo |
| D607,561 | S | 1/2010 | Grohol et al. |
| D614,293 | S | 4/2010 | Nelson et al. |
| 7,750,202 | B2 | 7/2010 | Niemeyer |
| 7,943,813 | B2 | 5/2011 | Petryk et al. |
| 8,044,255 | B2 | 10/2011 | Potts et al. |
| 8,080,704 | B2 | 12/2011 | Uchida et al. |
| 8,197,455 | B2 | 6/2012 | Zander et al. |
| 8,231,590 | B2 | 7/2012 | Zander et al. |
| 8,346,621 | B2 | 1/2013 | Kaufman et al. |
| 2001/0031954 | A1 | 10/2001 | Jordan et al. |
| 2004/0015145 | A1 | 1/2004 | Miura et al. |
| 2005/0071742 | A1 | 3/2005 | Balinsky |
| 2005/0145523 | A1 | 7/2005 | Zander et al. |
| 2005/0154365 | A1 | 7/2005 | Zander et al. |
| 2005/0217791 | A1 | 10/2005 | Costello et al. |
| 2005/0283131 | A1 | 12/2005 | Zander et al. |
| 2006/0004333 | A1* | 1/2006 | Olson .................... 604/361 |
| 2006/0111684 | A1 | 5/2006 | Berba et al. |
| 2006/0247594 | A1 | 11/2006 | Nickel et al. |
| 2008/0005212 | A1 | 1/2008 | Levien |
| 2008/0058748 | A1 | 3/2008 | Seifert et al. |
| 2008/0294140 | A1 | 11/2008 | Ecker et al. |
| 2009/0012491 | A1 | 1/2009 | D'Addario et al. |
| 2009/0062764 | A1 | 3/2009 | MacDonald et al. |
| 2009/0157021 | A1 | 6/2009 | Sullivan et al. |
| 2010/0100067 | A1 | 4/2010 | Pugliese, III |
| 2012/0165771 | A1 | 6/2012 | Ruman et al. |

FOREIGN PATENT DOCUMENTS

| | | |
|---|---|---|
| EP | 1 306 069 A3 | 5/2003 |
| EP | 1 693 034 A1 | 8/2006 |
| WO | WO 03/013406 A1 | 2/2003 |
| WO | WO 03/013409 A1 | 2/2003 |
| WO | WO 2009/027856 A2 | 3/2009 |
| WO | WO 2009/027856 A3 | 3/2009 |
| WO | WO 2011/027295 A2 | 3/2011 |
| WO | WO 2011/027295 A3 | 3/2011 |

OTHER PUBLICATIONS

Abstract of Japanese Patent—JP 2008173506, Jul. 31, 2008, 2 pages.
Chinese Design Patent—CN 301679954 S dated Sep. 21, 2011, 3 pages.
Taiwanese Design Patent—TW D112475, Aug. 11, 2006, 3 pages.
European Design Patent—EM 000406731-0005, Aug. 14, 2007, 2 pages.
European Design Patent—EM 000854203-0001, Feb. 20, 2008, 2 pages.
European Design Patent—EM 000854203-0002, Feb. 20, 2008, 2 pages.
Abstract of Russian Patent—RU2290154, Dec. 27, 2006, 1 page.

* cited by examiner

ABSORBENT ARTICLE HAVING ASYMMETRIC PRINTED PATTERNS FOR PROVIDING A FUNCTIONAL CUE

BACKGROUND OF THE INVENTION

Absorbent articles, such as sanitary napkins, pantiliners, and incontinent pads are devices that are typically worn in the crotch region of an undergarment. Sanitary napkins and pantiliners are, for example, worn by women in a pair of panties that is normally positioned between the wearer's legs, adjacent to the perineum area. Sanitary napkins and pantiliners are designed to absorb and retain body fluids or discharges (e.g., menses) from the body of women and to prevent body and clothing from soiling. The menstrual period is very troublesome for women and many women experience mood swings during the period. Conventional sanitary napkins have a white color or a simple combination of light colors to provide a clean appearance. Because of the appearance, such sanitary napkins normally do not impact a woman's feelings in that they do not help to decrease or change her mood during the menstruation period. Various attempts have been made to address this problem. U.S. Patent Application Publication No. 2004/0015145 to Miura, et al., for example, describes a sanitary napkin having a graphic printed onto either the body-contacting layer or the garment contacting layer, and that can be seen through the body contacting layer. The body-contacting layer is said to have a certain light transmittance so that the graphic can be seen by a woman through the layer to improve her mood during menstruation. Unfortunately, however, such "mood" driven designs do not address other practical concerns of women. For instance, one problem experienced by many women is that leakage can sometimes occur around the periphery of a product, which may become visible upon disposal, and lead to embarrassment for the consumer, and a general loss of confidence in the product. Another concern of women is the need to recognize when a pad is soiled, despite the desire to have aesthetically pleasing designs. While Miura, et al. references conventional mechanisms (e.g., embossed walls or channels) for preventing such leakage, it does not offer guidance for when conventional mechanisms fail and leakage occurs.

As such, a need currently exists for an absorbent article that is both visually appealing, communicates to a consumer that a pad is working, or when it is soiled, but also helps masks leakage of bodily fluids at certain locations, thereby offering to reduce uncomfortable feelings/embarrassment with excessive menstruation. There is therefore a need for absorbent articles that provide functional cues to the user, while avoiding embarrassment.

SUMMARY OF THE INVENTION

In accordance with one embodiment of the present invention, an absorbent article is disclosed that defines a longitudinal centerline and a transverse centerline. The article comprises a topsheet, baffle, and an absorbent core disposed between the topsheet and the baffle. The topsheet and baffle extend outwardly from a circumferential edge of the absorbent core and into a first longitudinally extending periphery portion located on one side of the longitudinal centerline, a second longitudinally extending periphery portion located along another side of the longitudinal centerline, a third laterally extending periphery portion located on one side of the transverse centerline and between respective inboard dimensions of the first peripheral zone and the second peripheral zone, and a fourth laterally extending peripheral portion located on another side of the transverse centerline and between respective inboard dimensions of the first and second peripheral zones. A first transition zone extends circumferentially about an interior zone adjacent to the third peripheral zone and a second transition zone extends circumferentially about the interior zone adjacent to the fourth peripheral zone. A first printed pattern of discrete graphical objects is located within the first peripheral zone and extends at least partially into the first transition zone, the second transition zone, or both. A second printed pattern of discrete graphical objects is located within the second peripheral zone and extends at least partially into the first transition zone, the second transition zone, or both. The first printed pattern is asymmetrical with respect to the second printed pattern about both the longitudinal and transverse centerlines. The first printed pattern and the second printed pattern are visible from a body facing surface of the topsheet. A majority of the interior zone is free of printed graphical objects.

In accordance with another embodiment of the present invention, a feminine care absorbent article is disclosed that comprises a passive masking component and an active masking component. The passive masking component includes a first printed pattern of discrete graphical objects located within a first peripheral zone and extending at least partially into a first transition zone and/or second transition zone of the absorbent article, and a second printed pattern of discrete graphical objects located within a second peripheral zone and extending at least partially into the first transition zone and/or second transition zone. The first printed pattern is asymmetrical with respect to the second printed pattern about both longitudinal and transverse centerlines, and the first printed pattern and the second printed pattern are visible from a body facing surface of a topsheet. A majority of the interior zone of the absorbent article is also free of printed graphical objects. Furthermore, the active masking component is located within the first peripheral zone, the second peripheral zone, the first transition zone, the second transition zone, or a combination thereof.

In one embodiment, an active stain masking component may be employed that includes a decolorizing composition. The decolorizing composition may include an agglutinating agent, oxidizing agent, or a combination thereof. The decolorizing composition may be disposed within the first transition zone, second transition zone, or both.

Other features and aspects of the present invention are discussed in greater detail below.

BRIEF DESCRIPTION OF THE FIGURES

A full and enabling disclosure of the present invention, including the best mode thereof, directed to one of ordinary skill in the art, is set forth more particularly in the remainder of the specification, which makes reference to the appended figures in which.

Figure 1:
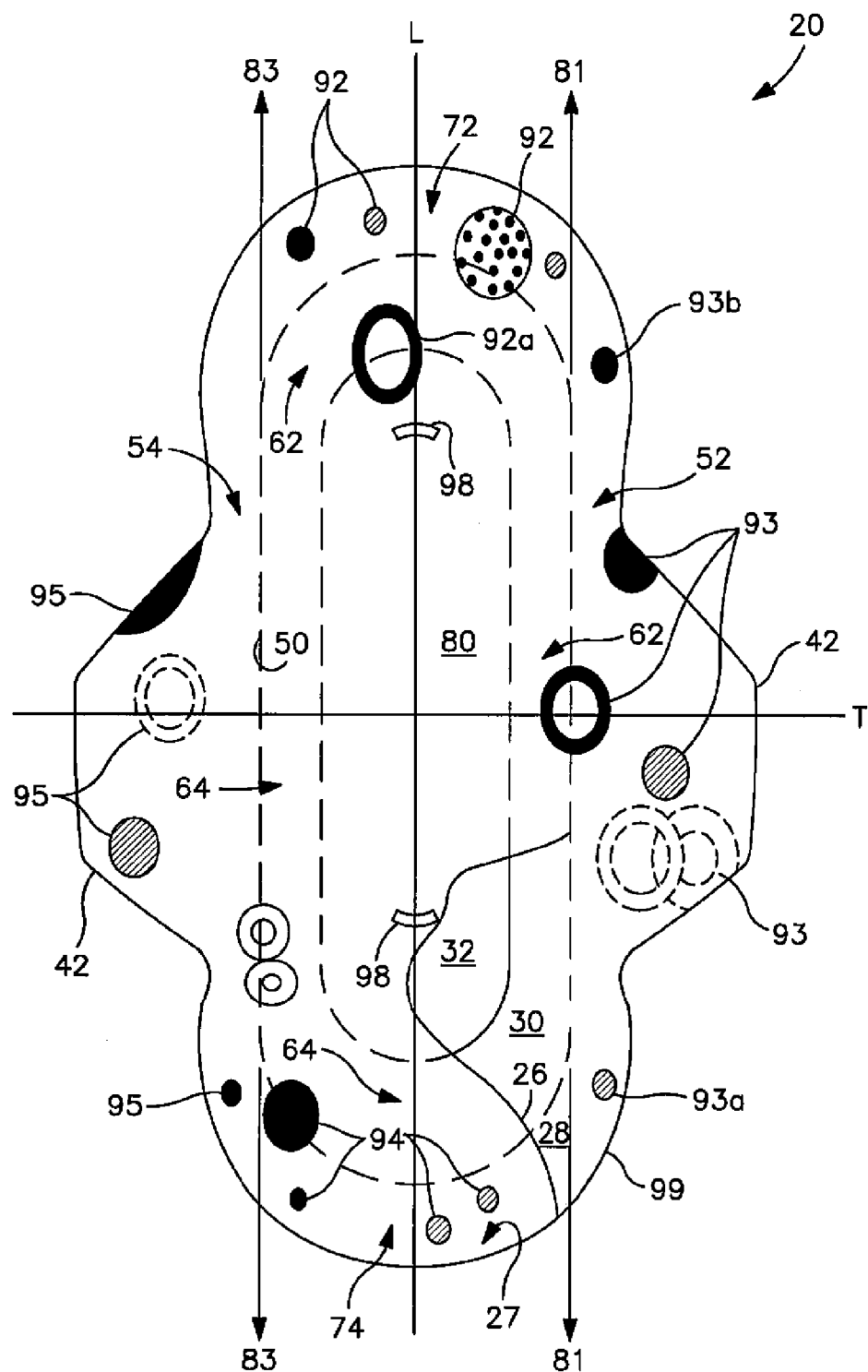
FIG. 1 is a top view of one embodiment of the absorbent article of the present invention.

Repeat use of reference characters in the present specification and drawings is intended to represent same or analogous features or elements of the invention.

DETAILED DESCRIPTION OF REPRESENTATIVE EMBODIMENTS

Definitions

As used herein, the term "body-facing surface" generally refers to an outwardly facing surface of an absorbent article that is intended to be disposed toward or placed adjacent to the body of a wearer during ordinary use. This surface may be defined by a topsheet, which also includes an opposing inwardly facing surface.

As used herein, the term "garment-facing surface" generally refers to an outwardly facing surface of an absorbent article that is intended to be disposed away from the body of a wearer during ordinary use. The surface is typically placed adjacent to the wearer's undergarments when the article is worn. This surface may be defined by a baffle, which also includes an opposing inwardly facing surface.

Detailed Description

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

Generally speaking, the present invention is directed to a feminine care absorbent article that contains multiple printed patterns of graphical objects visible from a body facing surface. The layout and design of the patterns are carefully selected in the present invention to achieve a synergistic masking effect that helps visually disguise the presence of bodily fluids or stains around the periphery of the article. Such "passive" stain masking is achieved, in part, through the use of printed patterns that are distributed in an asymmetric manner about both the longitudinal and transverse centerlines of the article. Asymmetry may be provided in a variety of ways, such as through the use of objects of different sizes, colors, shapes, and designs. Among other things, the asymmetrical nature of the patterns allows the color of the bodily fluid to better blend with the visual nature of the patterns, and also draws the user's focus away from the areas in which any stains are located. In addition to such asymmetric distribution, the printed patterns are also strategically positioned within the article to produce the desired optical impact. Namely, the patterns are located at or near the periphery of the article and at least partially extend into portions of the body facing surface that overlie the absorbent core. Once again, this partial overlap into the absorbent core region helps further improve the capacity of the article to "passively" mask stains.

The present inventors have also discovered another aspect of the synergistic design of patterns is to balance the optical effects of "passive" stain masking with other functional cues. More particularly, while stain masking is an important characteristic, equally important is the ability to detect whether the absorbent article is functioning properly, or whether it needs to be changed. In this regard, the pattern design of the present invention is such that a majority of an interior zone of the absorbent article is generally free of printed graphical objects, in addition to providing the user the ability to better detect the presence of bodily fluids during use, the absence of printed objects in certain areas of the article also further enhances the overall distinctive nature of the patterns, and imparts a feeling of cleanliness to the use for that portion of the product that will be in contact with the user's most intimate areas.

Referring to FIG. 1, one particular embodiment of the feminine care absorbent article 20 of the present invention will now be described in more detail. As shown, the feminine care absorbent article 20 (e.g., feminine care pad or napkin) includes a topsheet 26, a baffle 28, and an absorbent core 30 positioned between the topsheet 26 and the baffle 28. The topsheet 26 defines a body-facing surface 27 of the absorbent article 20. The absorbent core 30 is positioned inwardly from the outer periphery of the absorbent article 20 and includes a body-facing side positioned adjacent the topsheet 26 and a garment-facing surface positioned adjacent the baffle 28. Typically, the topsheet 26 and the baffle 28 are joined by adhesive bonding, ultrasonic bonding, or any other suitable joining method known in the art, the sealed edges defining an overall sealed peripheral edge 99 of the article 20. The article 20 may take on various geometries but will generally have opposite lateral sides and longitudinal ends.

The topsheet 26 is generally designed to contact the body of the user and is liquid-permeable. The liquid permeable topsheet 26 has an outwardly facing surface that may contact the body of the wearer and receive aqueous fluids from the body. The topsheet 26 is provided for comfort and conformability and functions to direct bodily exudates away from the body, through the topsheet 26 and toward the absorbent core 30. The topsheet 26 retains little or no liquid in its structure so that it provides a relatively comfortable and non-irritating surface next to the tissues within the vestibule of a female wearer. The topsheet 26 can be constructed of any woven or nonwoven material that is easily penetrated by bodily exudates contacting the surface of the baffle. Examples of suitable materials include rayon, bonded carded webs of polyester, polypropylene, polyethylene, nylon, or other heat-bondable fibers, polyolefins, such as copolymers of polypropylene and polyethylene, linear low-density polyethylene, and aliphatic esters such as polylactic acid. Finely perforated film webs and net material can also be used. A specific example of a suitable topsheet material is a bonded carded web made of polypropylene and polyethylene such as that used as topsheet stock for KOTEX® pantiliners and obtainable from Sandler Corporation (Germany). U.S. Pat. No. 4,801,494 to Datta, et al. and U.S. Pat. No. 4,908,026 to Sukiennik, et al. teach various other topsheet materials that may be used in the present invention.

The topsheet 26 may also contain a plurality of apertures (not shown) formed therethrough to permit body fluid to pass more readily into the absorbent core 30. The apertures may be randomly or uniformly arranged throughout the topsheet 26, or they may be located only in the narrow longitudinal band or strip arranged along the longitudinal axis of the absorbent article 20. The apertures permit rapid penetration of body fluid down into the absorbent core 30. The size, shape, diameter and number of apertures may be varied to suit one's particular needs.

The baffle 28 is generally liquid-impermeable and designed to face the inner surface, i.e., the crotch portion of an undergarment (not shown). The baffle 28 may permit a passage of air or vapor out of the absorbent article 20, while still blocking the passage of liquids. Any liquid-impermeable material may generally be utilized to form the baffle 28. For example, one suitable material that may be utilized is a microporous polymeric film, such as polyethylene or polypropylene. In particular embodiments, a polyethylene film is utilized that has a thickness in the range of about 0.2 mils to about 5.0 mils, and particularly between about 0.5 to about 3.0 mils. A specific example of a baffle material is a polyethylene film such as that used in KOTEX® pantiliners and obtainable from Pliant Corporation, Schaumburg, Ill., USA.

As indicated above, an absorbent core 30 is positioned between the topsheet 26 and the baffle 28 that provides capacity to absorb and retain bodily exudates. The absorbent core 30 may be formed from a variety of different materials and contain any number of desired layers. For example, the core 30 typically includes one or more layers of an absorbent web material of cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic and hydrophilic materials, pigments, lotions, odor control agents or the like, as well as combinations thereof. In a particular embodiment, the absorbent web material includes a matrix of cellulosic fluff, and may also include superabsorbent material. The cellulosic fluff may comprise a blend of wood pulp fluff. One preferred type of fluff is identified with the trade designation NB 416 , available from Weyerhaeuser Corp., and is a bleached, highly absorbent wood pulp containing primarily soft wood fibers. The absorbent materials may be formed into a web structure by employing various conventional methods and techniques. For example, the absorbent web may be formed with a dry-forming technique, an air forming technique, a wet-forming technique, a foam-forming technique, or the like, as well as combinations thereof. A coform nonwoven material may also be employed. Methods and apparatus for carrying out such techniques are well known in the art.

The topsheet 26 may be maintained in secured relation with the absorbent core 30 by bonding all or a portion of the adjacent surfaces to one another. A variety of bonding mechanisms known to one of skill in the art may be utilized to achieve any such secured relation. Examples of such mechanisms include, but are not limited to, the application of adhesives in a variety of patterns between the two adjoining surfaces, entangling at least portions of the adjacent surface of the absorbent with portions of the adjacent surface of the cover, or fusing at least portions of the adjacent surface of the cover to portions of the adjacent surface of the absorbent The topsheet 26 typically extends over the upper, bodyside surface of the absorbent core 30, but can alternatively extend around the article to partially or entirely, surround or enclose the absorbent core. Alternatively, the topsheet 26 and the baffle 28 can have peripheral margins that extend outwardly beyond the terminal, peripheral edges of the absorbent core 30, and the extending margins can be joined together to partially or entirely, surround or enclose the absorbent core.

Although not required, the absorbent article 20 may also contain other additional layers as is known in the art. In FIG. 1, for example, a liquid-permeable intake layer 32 is positioned vertically between the topsheet 26 and the absorbent core 30. The intake layer 32 may be made of a material that is capable of rapidly transferring, in the z-direction, body fluid that is delivered to the topsheet 26. The intake layer 32 may generally have any shape and/or size desired. In one embodiment, the intake layer 32 has a rectangular shape, with a length equal to or less than the overall length of the absorbent article 20, and a width less than the width of the absorbent article 20. For example, a length of between about 150 mm to about 300 mm and a width of between about 10 mm to about 60 mm may be utilized. Any of a variety of different materials are capable of being used for the intake layer 32 to accomplish the above-mentioned functions. The material may be synthetic, cellulosic, or a combination of synthetic and cellulosic materials. For example, airlaid cellulosic tissues may be suitable for use in the intake layer 32. The airlaid cellulosic tissue may have a basis weight ranging from about 10 grams per square meter (gsm) to about 300 gsm, and in some embodiments, between about 40 gsm to about 150 gsm. The airlaid tissue may be formed from hardwood and/or softwood fibers. The airlaid tissue has a fine pore structure and provides an excellent wicking capacity, especially for menses.

The absorbent article 20 may also contain a transfer delay layer (not shown) positioned between the intake layer 32 and the absorbent core 30. The transfer delay layer may contain a material that is substantially hydrophobic, such as a nonwoven web composed of polypropylene, polyethylene, polyester, etc. One example of a material suitable for the transfer delay layer is a spunbond web composed of polypropylene, multi-lobal fibers. Further examples of suitable transfer delay layer materials include spunbond webs composed of polypropylene fibers, which may be round, tri-lobal or poly-lobal in cross-sectional shape and which may be hollow or solid in structure. Typically the webs are bonded, such as by thermal bonding, over about 3% to about 30% of the web area. Other examples of suitable materials that may be used for the transfer delay layer 36 are described in U.S. Pat. No. 4,798,603 to Meyer, et al. and U.S. Pat. No. 5,248,309 to Serblak, et al. To adjust performance, the transfer delay layer may also be treated with a selected amount of surfactant to increase its initial wettability. The transfer delay layer typically has a basis weight less than that of the other absorbent members. For example, the basis weight of the transfer delay layer 36 is typically less than about 250 grams per square meter (gsm), and in some embodiments, between about 40 gsm to about 200 gsm.

The absorbent article 20 may also include laterally extending wing portions 42 that may be integrally connected to side regions along the intermediate portion of the article. For example, the wing portions 42 may be separately provided members that are subsequently attached or otherwise operatively Joined to the intermediate portion of the article. In other configurations, the wing portions may be unitarily formed with one or more components of the article. As representatively shown in FIG. 1, for example, either or both wing portions 42 may be formed from a corresponding, operative extension of the material employed to form the topsheet 26. Alternatively, either or both wing portions 42 may be formed from a corresponding, operative extension of the material employed to form the baffle 28, or formed from a corresponding, operative combination of the topsheet and baffle materials.

Regardless of the particular configuration of the layers used in forming the absorbent article 20, a plurality of objects are printed in patterns so that they are visible from the body-facing surface 27. The particular patterns are carefully selected to provide a unique visual appearance that both aids in "passive" stain masking and provides a functional cue to the user. More particularly, as shown in FIG. 1, the topsheet 26 and baffle 28 extend outwardly from a circumferential edge 50 of the absorbent core 30 and into a first longitudinally extending periphery portion 52 located on side of a longitudinal centerline "L" and a second longitudinally extending periphery portion 54 located along another side of the longitudinal centerline. The topsheet 26 and baffle 28 may also extend outwardly from the circumferential edge 50 into a third laterally extending periphery portion 72, which is located on one side of a transverse centerline "T", and a fourth laterally extending periphery portion 74 located along another side of the transverse centerline. As shown, the third periphery portion 72 and fourth peripheral portion 74 are located between longitudinal inboard dimensions 81 and 83 of the first peripheral zone 52 and the second peripheral zone 54, respectively. Although not necessarily required, in the embodiment shown in FIG. 1, the periphery portions 52, 54, 72, and 74 together extend around the entire periphery of the article to an edge 99.

To help reduce the visibility of stains around the outer periphery, particularly at the lateral edges, the present inventors have discovered that a pattern of graphical objects may be printed within both the first peripheral zone 52 and the second peripheral zone 54. The patterns may be printed on any layer of the article 20, so long as they are visible from the body-facing surface 27. For example, patterns may be printed on the outwardly facing surface of the topsheet 26 so that they are readily visible. Likewise, patterns may be printed onto the inwardly facing surface of the baffle 28 in such a manner that they still remain visible from the body-facing surface 27. Regardless, a first printed pattern of discrete graphical objects 93 is located within the first peripheral zone 52 and a second printed pattern of discrete graphical objects 95 is located within the second peripheral zone 54.

As shown, the first and second printed patterns are asymmetrical about both the longitudinal centerline "L" and the transverse centerline "T." The use of asymmetrical printed patterns in longitudinally extending periphery portions can help provide a unique visual appearance and also to help mask stains in those locations where such masking is most needed. It should be understood, however, that the presence of printed patterns is by no means limited to these locations. Referring again to FIG. 1, for example, a third printed pattern of discrete graphical objects 92 may also be located within the third peripheral zone 72 and a fourth pattern of discrete graphical objects 94 may be located within the fourth peripheral zone 74. As described above, these patterns may be printed onto the baffle 28, topsheet 26, etc., so long as they are visible to the user from the body facing surface 27. The third pattern may also be asymmetrical with respect to the fourth pattern about both the longitudinal and transverse centerlines. In this manner, the entire periphery may possess an overall asymmetrical appearance, which is both desirable for "pre-use" visual appearances as well as to impart "post-use" passive masking of stains. Of course, it should be understood that the presence of a pattern around the entire periphery is by no means required. In certain embodiments, for example, the third peripheral zone 72 and/or fourth peripheral zone 74 may be free of printed graphical objects.

In addition to selectively controlling the visual appearance of the printed patterns along the periphery, the present inventors have also discovered that the capacity to passively mask stains can be even further enhanced by extending at least a portion of the patterns into regions of the body facing surface that overlie the absorbent core. Such overlap into the absorbent core region helps further improve the capacity of the article to "passively" mask stains. In FIG. 1, for example, the absorbent article defines a first transition zone 62 that extends circumferentially about an interior zone 80 on one side of the transverse centerline "T" so that it is adjacent to the third peripheral zone 72 and to both longitudinal peripheral zones 52 and 54. A second transition zone 64 likewise extends circumferentially about the interior zone 80 on the other side of the transverse centerline "T" so that it is adjacent to the fourth peripheral zone 74 and to both longitudinal peripheral zones 52 and 54. In the illustrated embodiment, the interior zone 80 is the visible region of the article 20 (e.g., topsheet 26, baffle 28, or absorbent core 30) that corresponds to the intake layer 32, and the transition zones 62 and 64 are the visible regions of the article 20 that correspond to the portions of the core 30 that extend beyond the intake layer 32. Although not required, the transition zones may thus together extend around the entire periphery of the interior zone 80. As reflected in FIG. 1, the interior zone 80 typically constitutes from about 25% to about 75%, and in some embodiments, from about 35% to about 65% of the combined surface area of the interior and transition zones.

Regardless of the particular configuration, the presence of printed patterns within one or more of the transition zones can help give the overall appearance of a more cohesive or coordinated appearance, while minimizing distractions from the graphical elements purpose of providing the functional cue or a fun or amusing appearance. For instance, referring again to FIG. 1, the first printed pattern of graphical objects 93 and second printed pattern of graphical objects 95 both extend into the first transition zone 62 and the second transition zone 64. Once again, this may be accomplished by printing objects onto the baffle 28, topsheet 26, etc. in such a manner that the overall patterns are asymmetric about both the longitudinal centerline "L" and transverse centerline "T." If desired, the third printed pattern of graphical objects 92 may extend into the first transition zone 62 and/or and the fourth printed pattern of graphical objects 94 may extend into the second transition zone 64.

Asymmetry in the printed patterns described above may be provided in a variety of ways, such as through the use of objects of different sizes, colors, shapes, and designs. Such asymmetry accomplishes the dual functions of providing a unique and distinctive "pre-use" visual appearance, and providing a "post-use" visual appearance that can passively mask stains after the product has been used. The asymmetry indicates that the patterns do not have simple symmetry like reflection, rotational, and translational symmetries, and preferably do not have Glide reflection, roto-reflection, helical, or non-isometric symmetries. While being asymmetrical, the patterns may nevertheless provide an asymmetrical balance to the extent that several smaller graphical objects on one side may be "balanced" by a large graphical object on the other side, or smaller objects may be placed further away from the center than larger objects. Alternatively, a darker object may be similarly balanced by several lighter objects. It also should be noted that although the graphical objects 93 and 95 are shown herein as possessing relatively simple shapes, this is merely for exemplary purposes. Virtually any shape or design may be employed, such as dots, ovals, triangles, squares, rectangles, flowers, butterflies, stars, hearts, spirals, double spirals, clothold curves, comu spirals, polynomial double spirals, Euler's double spirals, parametric double spirals, etc. In fact, it is generally preferable that the graphical objects are more complicated in nature and that they possess some degree of curvature and color to provide a more complex visual perception and aid in the overall masking effect of the article. For example, FIGS. 4-9 generically illustrate more complex graphical objects that may be employed in the present invention.

The specific graphical objects may also be selected so that, although asymmetrical, they are visually coordinated with the surrounding environment to provide a perception that the product will perform better. The surrounding environment may, for instance, be the packaging (e.g., wrapper, bag, etc.) within which the absorbent article is initially provided, such as described in U.S. Patent Publication No. 2005/0154365 to Zander, et al., which is incorporated herein in its entirety by reference thereto for all purposes. The objects may also be visually coordinated with a garment, such as described in U.S. Patent Publication No. 2008/0058748 to Seifert, et al., which is also incorporated herein in its entirety by reference thereto for all purposes. Visually coordinated graphical objects are those in which two or more visual characteristics either match or are caused to match.

In certain cases, the graphical objects may also be arranged to impart an optical illusion when viewed from a particular focal point of the user. For instance, the arrangement of the graphical objects relative to one another may form an optical illusion of motion perceivable as at least one of the objects appearing to move away from an edge of the body. Exemplary objects for providing such an illusionary pattern may include geometric, spiral, anomalous motion, rotational, color change, peripheral drift, positive after image blurs, scintillation grid, stereopsis and chromosteropsis, contraction and expansion, contrast polarities, convection, chromatic assimilation, etc., such as described in U.S. Patent Publication Nos. 2009/0157021 to Sullivan, et al. and 2005/0268371 to Meekins, which are incorporated herein in their entirety by reference thereto for all purposes. In another embodiment, graphical objects of different shades may be employed to create a perception of depth within the absorbent article by a user looking upon the viewing surface of the topsheet. Such illusionary patterns are described in U.S. Patent Publication No. 2003/0114811 to Christon, et al., which is incorporated herein in its entirety by reference thereto for all purposes. Regardless of the mechanism employed, the optional illusions can cause the user to perceive the stain to be different or deeper in the product that what it actually is, and thus enhance passive masking.

The graphical objects referenced above are generally passive to the extent that they do not change during use of the product. In certain instances, however, it may be desired to incorporate one or more active graphical objects in the printed patterns to further enhance the "post use" impact on the user. For example, one or more active graphical objects may be employed that "disappear" or "appear" from view at a certain time. Active graphics may be employed that are soluble in aqueous solutions and therefore fade in color when contacted with urine. Such graphics are described, for instance, in U.S. Pat. No. 6,307,119 to Cammarota, et al. and U.S. Pat. No. 4,022,211 to Timmons, et al., which are incorporated herein in their entirety by reference thereto for all purposes. Active graphics may also be employed that appear over time due to exposure to time intervals, temperature levels, oxygen levels, etc., such as described in U.S. Pat. No. 5,058,088 to Haas, et al.; U.S. Pat. No. 5,053,339 to Patel; U.S. Pat. No. 5,045,283 to Patel; U.S. Pat. No. 4,987,849 to Sherman; U.S. Pat. No. 4,903,254 to Haas; U.S. Pat. No. 4,812,053 to Bhattacharjee; and U.S. Pat. No. 4,292,916 to Bradley et al., which are incorporated herein in their entirety by reference thereto for all purposes. In addition to enhancing masking, such interactive graphical objects may also provide additional performance cues to the user. For example, appearing graphical objects may serve as wetness or void volume indicator, such as described in U.S. Pat. No. 7,322,472 to Swiecicki, et al., which is incorporated herein in its entirety by reference thereto for all purposes.

While the presence of asymmetric patterns within the peripheral and transition zones can help provide the desired coordinated visual appearance, it is likewise desired to keep a majority of the interior zone free of graphical objects so that the user will be provided a distinctive visual cue that the product is performing as expected. More specifically, at least 50% of the area of the bodily-facing surface located within the interior zone is free of printed graphical objects. In certain embodiments, at least 60% of the surface area, and in some embodiments, from 75% to 100% of the surface area of the interior zone is free of printed graphical objects. Of course, a portion of the interior zone may still contain graphical objects. In the embodiment shown in FIG. 1, for example, a graphical object 92a is shown within the interior zone. When present, such graphical objects may be distributed symmetrically or asymmetrically about the transverse and/or longitudinal centerlines. It should be understood that the term "free of printed graphical objects" does not preclude the presence of any printed ink. The phrase simply means that graphical objects (e.g., flowers, spirals, dots, etc.) having a defined shape and size are not located within the given area. For example, the entire surface may be printed with a colored ink, and thereafter, a pattern of graphical objects may be printed thereon that covers less than 50% of the surface area. Despite the fact that the entire surface contains a printed ink, the majority of the interior zone is still considered to be free of printed graphical objects.

Generally speaking, the printed "patterns" of the present invention include a set of graphical objects within a given area. However, as mentioned, the graphical objects need not be printed on the same surface within this area. For example, in the embodiment shown in FIG. 1, at least a portion of graphical objects 93 are printed onto the baffle 28 as graphically illustrated by object 93a. The object 93a may still be visible on the bodily-facing surface 27 through the use of a topsheet 26 having a degree of light transmittance. Within the same pattern, another portion of the objects 93 may also be printed onto the topsheet 26 as graphically illustrated by object 93b. In addition to enhancing manufacturing flexibility, the use of patterns with graphical objects located on multiple surfaces can provide a distinctive visual appearance that facilitates masking of stains and assists in the provision of other functional cues to the user. Regardless, the graphical objects together form a pattern that is visible and recognizable by the user.

Figure 2:
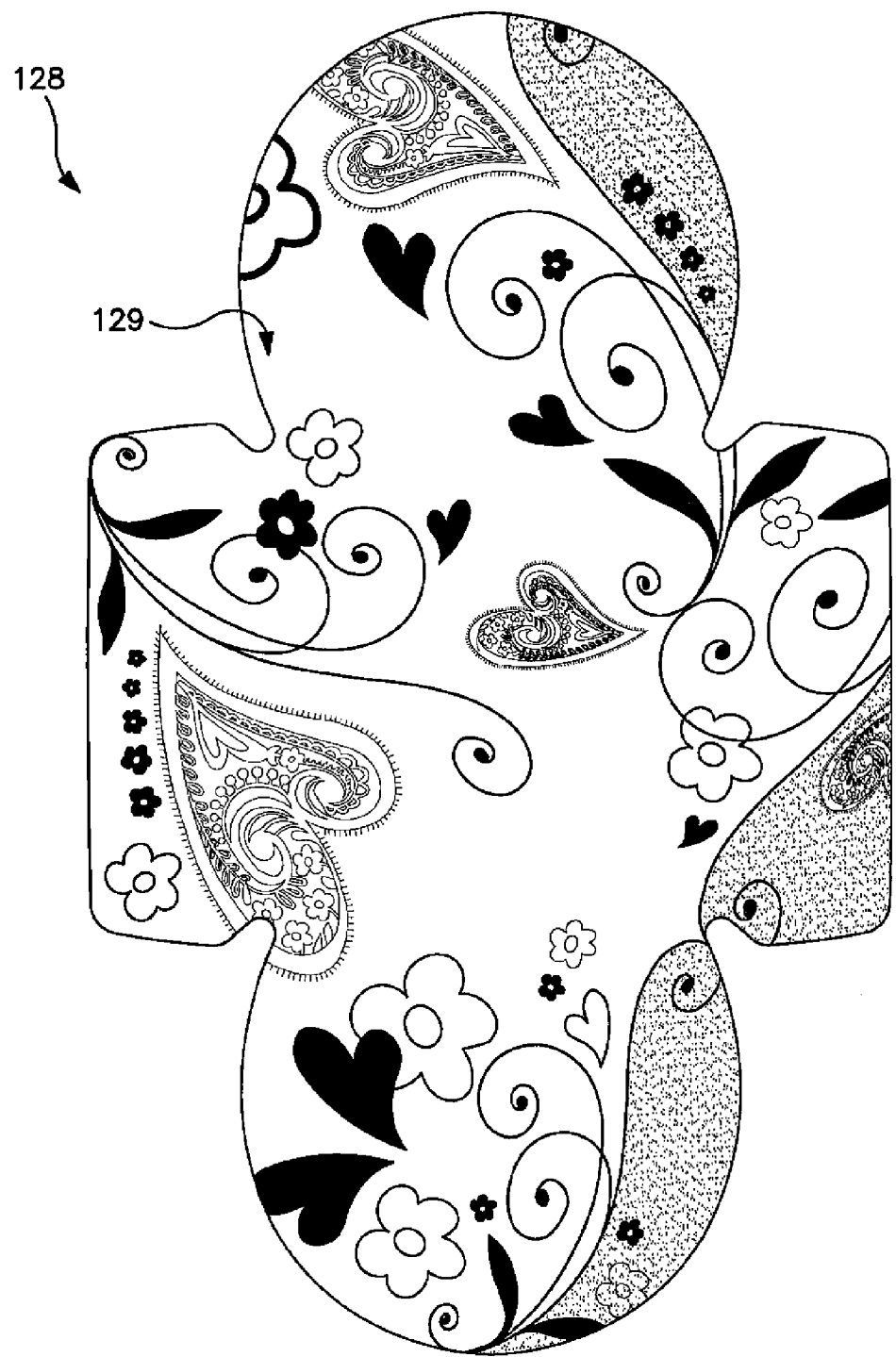
FIG. 2 is a top view of one embodiment of a baffle used in one embodiment of the absorbent article of the present invention.
Figure 3:
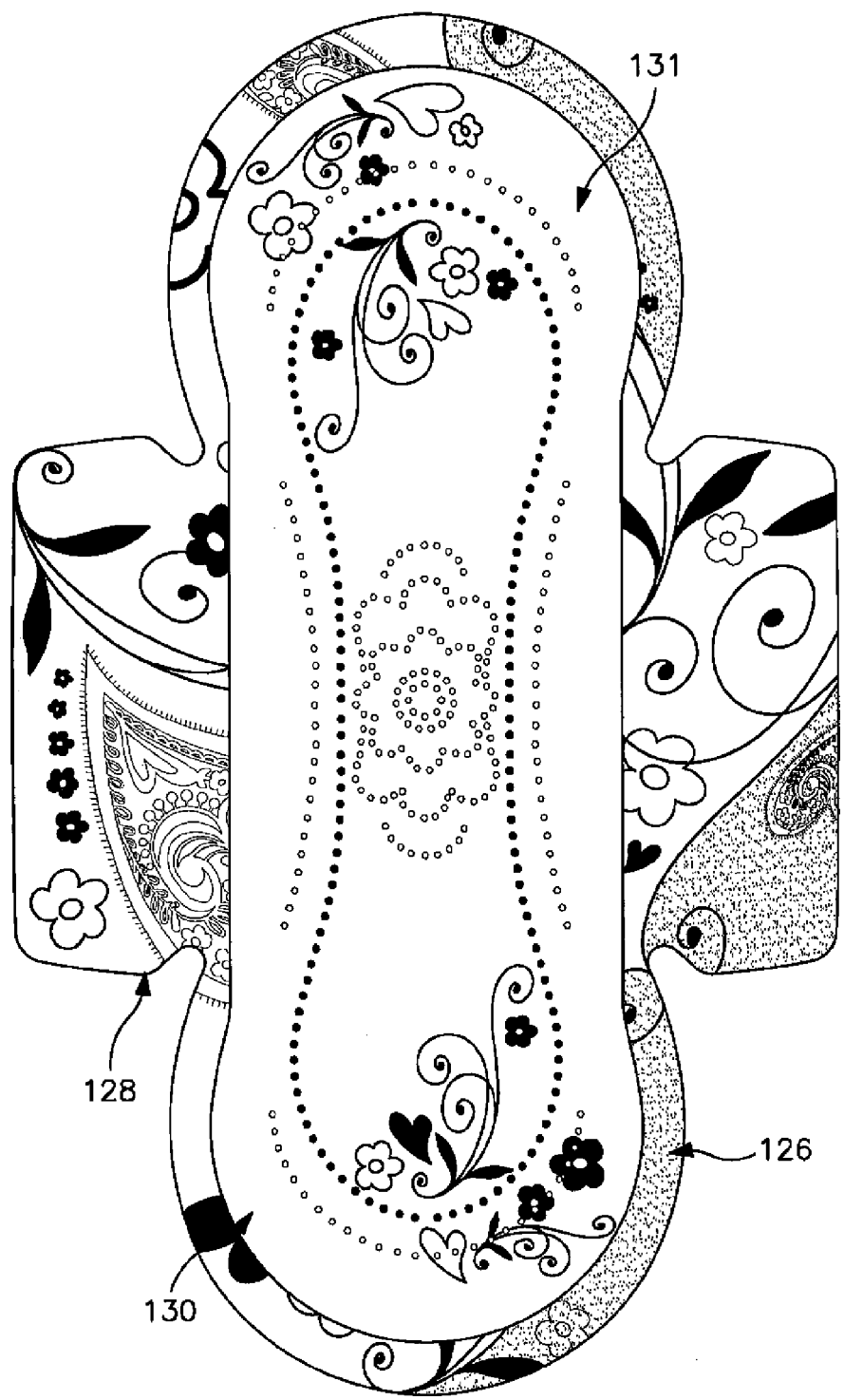
FIG. 3 is a top view of one embodiment of the absorbent article of the present invention that contains a topsheet positioned over the baffle of FIG. 2.
Figure 4:
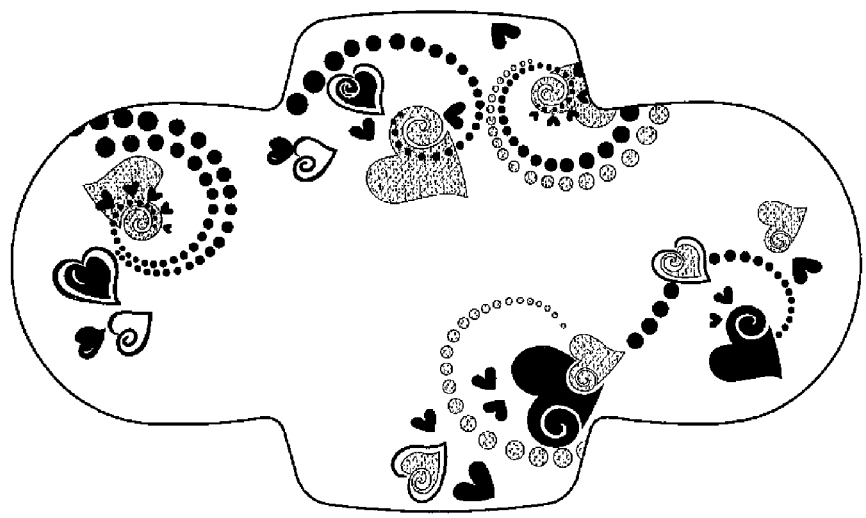
FIG. 4-9 illustrate various printed patterns that may be employed on a topsheet of the absorbent article of the present invention.
Figure 5:
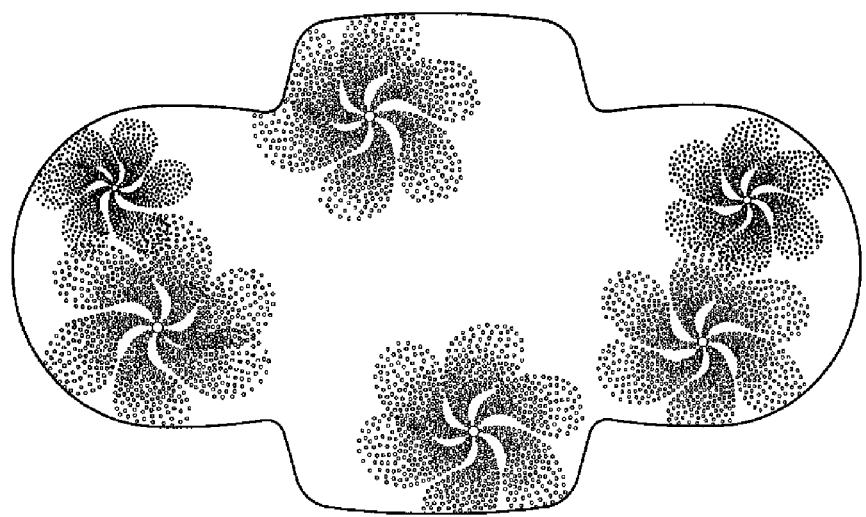
Figure 7:
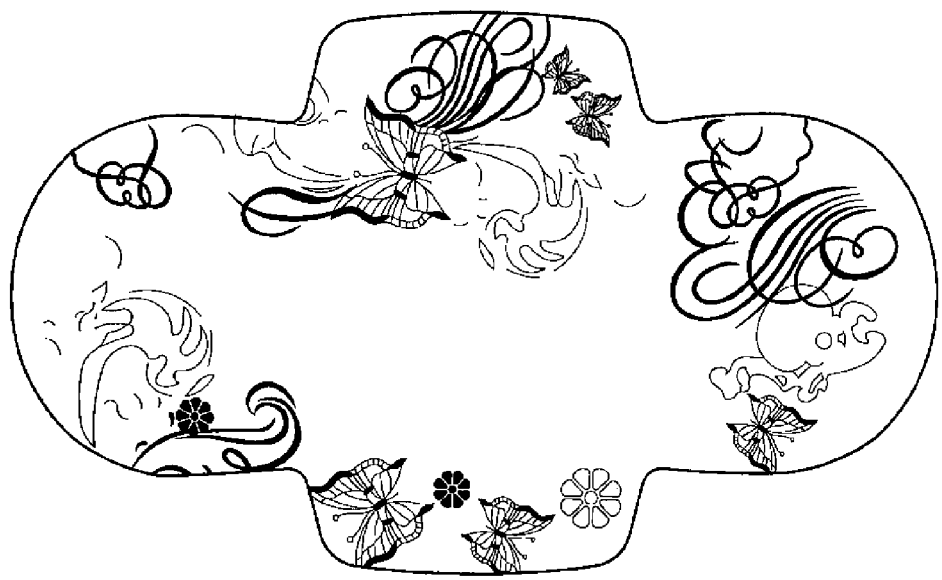
Figure 6:
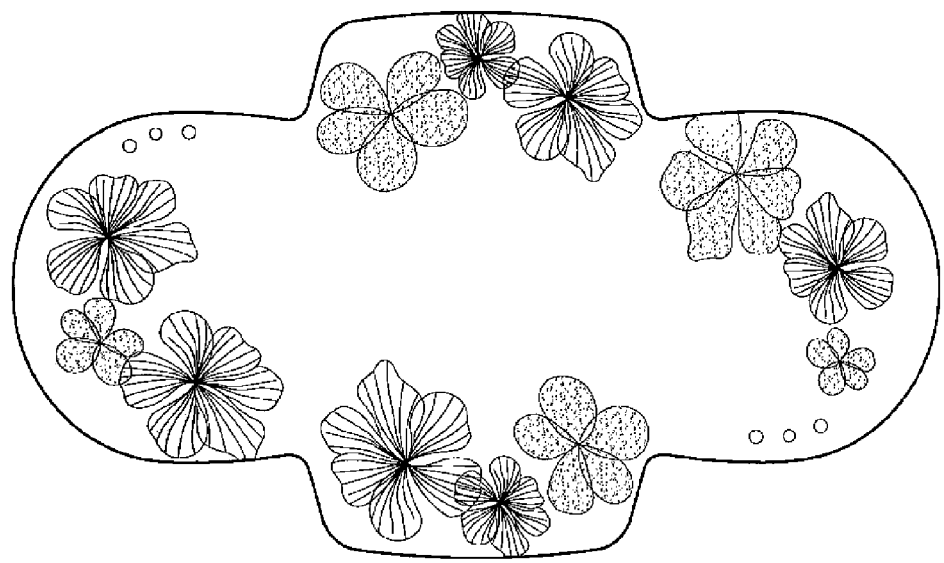
Figure 9:
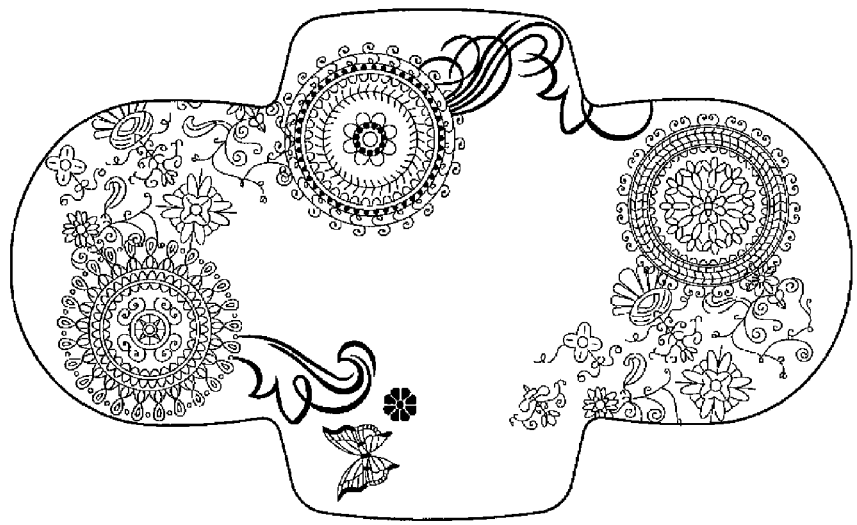
Figure 8:
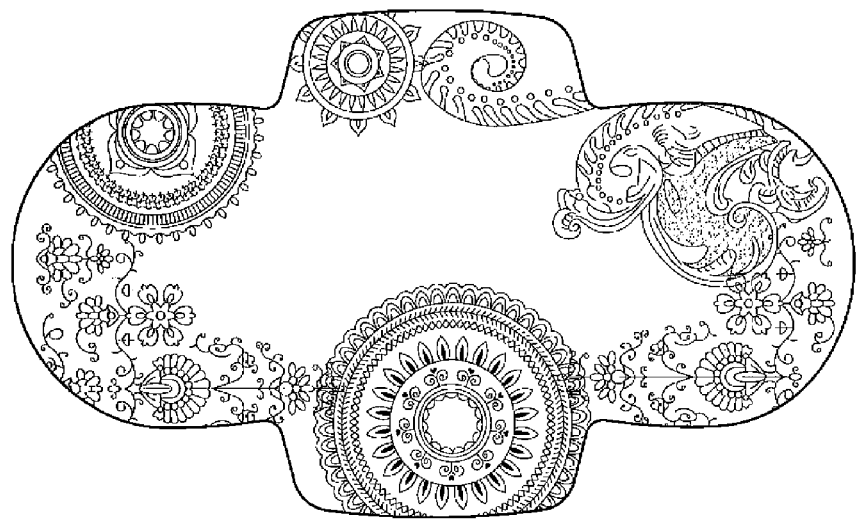

The ability to print patterns onto both the topsheet and baffle is better illustrated in FIGS. 2-3. Referring to FIG. 2, for example, one embodiment of a baffle 128 is shown that contains a surface 129 that faces inwardly toward the body during use. In this particular embodiment, the surface 129 is printed with multiple patterns of graphical objects around its periphery and interior. FIG. 3 shows the baffle 128 after it is covered by an absorbent core 130 and a topsheet 126 that defines a bodily-facing surface 131. Because the topsheet 128 is light transmissive, the graphical objects printed onto the baffle 128 remain visible from the bodily-facing surface 131, albeit in a lighter shade. However, at those locations where the absorbent core 130 covers the baffle 128, the graphical objects on the baffle 128 are not visible from the bodily-facing surface. Nevertheless, graphical objects are printed onto the topsheet 126 so that, together with the graphical objects on the baffle 128, a unique and distinctive arrangement of patterns is created.

If desired, other aspects of the absorbent article may also be controlled to enhance passive stain masking. For example, a reflective material (e.g., backing, pigment, etc.) can be employed in one or more layers of the article to enhance the light intensities emanating from the colored surfaces, while diminishing even further the perception of slight staining.

Examples of such reflective materials are described in more detail in WO 2003/013406 to Benecke, et al., which is incorporated herein in its entirety by reference thereto for all purposes. Opacifying agents (e.g., titanium dioxide, calcium carbonate, etc.) may likewise be employed to help mask absorbed fluids, such as described in U.S. Pat. No. 4,801,494 to Datta, et al., which is incorporated herein in its entirety by reference thereto for all purposes.

As emphasized above, the unique and distinctive pattern arrangement of the present invention enhances "passive" stain masking. The present inventors have discovered, however, that the use of an "active" masking component in combination with such unique patterns may have a synergistic impact on the user's overall experience with the product. For example, the active masking component can physically alter the color of the bodily fluid or direct it to a more hidden location in the article. In either case, the printed patterns of the present invention may be coordinated with the active masking component to enhance the desired visual impact.

In certain embodiments, for example, the active masking component may include one or more structural elements formed into a layer of the article to help guide the bodily fluid in the desired direction (e.g., along the bodyside surface of the article) to minimize the visibility of stains within the periphery, but yet still provide a visual cue regarding fit and leakage protection. Suitable structural elements may include, for instance, embossments, recessed areas, raised areas, apertures, etc. The particular arrangement of the structural elements is not generally critical. In one embodiment, for example, embossed channels are employed that deform the topsheet and selected portions of the absorbent core. The embossing pattern not only creates an aesthetically pleasing surface, but the channels facilitate intake of menses in that the fluid will tend to flow along the densified edges of the channels rather than pool on contact points of the topsheet 26. The embossed channels may be positioned adjacent the perimeter edges of the absorbent core in a symmetric or asymmetric manner. Referring to FIG. 1 again, for example, symmetric embossed channels 98 are shown that are provided within the interior zone 80 near the upper and lower circumferential edge of the intake layer 32.

In addition to embossed channels, other structural elements may also be employed to help guide the fluid and act as an "active" masking component. As an example, U.S. Pat. No. 5,614,295 to Quincy, III., et al., which is incorporated herein in its entirety by reference thereto, describes a fibrous web that is specifically configured to distribute liquid in the direction of the orientation of the fibers. The web is formed from a first zone of fibers treated with a surfactant and a second zone of fibers exposed to a corona field. Another suitable fluid guide may include a permeable sheet (e.g., nonwoven web) adsorbed with an amphiphilic protein (e.g., milk protein) to define a gradient distribution of an amphiphilic protein coating along at least one dimension of the permeable sheet. This provides controlled wettability along at least one dimension of the permeable, liquid flow control material. Such materials are described in more detail in U.S. Pat. No. 5,912,194 to Everhart, et al., which is incorporated herein in its entirety by reference thereto for all purposes. In yet another embodiment, the fluid guide may be a nonwoven web having a high basis weight and/or high denier, such as described in U.S. Pat. No. 4,892,534 to Datta, et al., which is incorporated herein in its entirety by reference thereto for all purposes. For example, the basis weight may range from about 0.5 to 1.0 ounces per square yard, and in some embodiments, from about 0.7 to 1.0 ounces per square yard, and the denier may range from about 3 to about 15, and in some embodiments, from about 4 to about 12. Such high basis weight and high denier webs contain large passageways that extend downward through the thickness of the web and have the ability to draw a greater quantity of bodily fluid away from the visible surface, thereby actively masking visible stains. Regardless of the particular mechanism employed, however, such fluid guides may help control or coordinate the stain pattern, thereby "actively" enhancing the masking effect of the present invention. The fluid guides may be employed in the center and/or periphery of the article as desired.

A chemical treatment may also be employed as an active masking component that alters the bodily fluid itself. In one embodiment, for example, the treatment may be a decolorizing composition that agglutinates (agglomerates) red blood cells in blood and menses and limits the extent that the red color of menses is visible. One such composition includes a surfactant, such as described in U.S. Pat. No. 6,350,711 to Potts, et al. which is incorporated herein in its entirety by reference thereto. Particular examples of such surfactants are Pluronic® surfactants (tri-block copolymer surfactant). Another suitable composition that can help agglutinate (agglomerate) the cells includes one or more inorganic salts that contain a polyvalent anion (e.g., divalent, trivalent, etc.), such as sulfate ($SO_4^{2-}$), phosphate ($PO_4^{3-}$), carbonate ($CO_3^{2-}$), oxide ($O^{2-}$), etc., and a monovalent cation, such as sodium ($Na^+$), potassium ($K^+$), lithium ($LI^+$), ammonium ($NH_4^+$), etc. Alkali metal cations are particularly desirable. Specific examples of salts formed from such ions include, for instance, disodium sulfate ($Na_2SO_4$), dipotassium sulfate ($K_2SO_4$), disodium carbonate ($Na_2CO_3$), dipotassium carbonate ($K_2CO_3$), monosodium phosphate ($NaH_2PO_4$), disodium phosphate ($Na_2HPO_4$), monopotassium phosphate ($KH_2PO_4$), dipotassium phosphate ($K_2HPO_4$), etc. Mixtures of the aforementioned salts may be particularly effective in facilitating physical separation of red blood cells. For instance, a mixture of disodium sulfate ($Na_2SO_4$) and monopotassium phosphate ($KH_2PO_4$) may be employed.

Besides agglutinating agents, the decolorizing composition may also alter the chemical structure of hemoglobin to change its color. Examples of such compositions are described in U.S. Patent Application Publication No. 2009/0062764 to MacDonald, et al., which is also incorporated herein in its entirety. More particularly, the composition includes an oxidizing agent that is generally capable of oxidizing hemoglobin or other substances responsible for an unwanted color of the bodily exudates. Suitable oxidizing agents may include, for instance, peroxygen bleaches (e.g., hydrogen peroxide, percarbonates, persulphates, perborates, peroxyacids, alkyl hydroperoxides, peroxides, diacyl peroxides, ozonides, supereoxides, oxo-ozonides, and periodates); hydroperoxides (e.g., tert-butyl hydroperoxide, cumyl hydroperoxide, 2,4,4-trimethylpentyl-2-hydroperoxide, dl-isopropylbenzene-monohydroperoxide, tert-amyl hydroperoxide and 2,5-dimethyl-hexane-2,5-dihydroperoxide); peroxides (e.g., lithium peroxide, sodium peroxide, potassium peroxide, ammonium peroxide, calcium peroxide, rubidium peroxide, cesium peroxide, stromtium peroxide, barium peroxide, magnesium peroxide, mercury peroxide, silver peroxide, zirconium peroxide, hafnium peroxide, titanium peroxide, phosphorus peroxide, sulphur peroxide, rhenium peroxide, iron peroxide, cobalt peroxide, and nickel peroxide); perborates (e.g., sodium perborate, potassium perborate, and ammonium perborate); persulphates (e.g., sodium persulphate, potassiumdlpersulphate, and potassium persulphate); and so forth. Other suitable oxidizing agents are omega-3 and -6 fatty acids, such as linoleic acid, α-linoleic acid, arachidonic acid, eicosapentaenoic acid, docosahexaenoic acid, eicosadienoinc acid, eicosatrienoic acid; etc.

Regardless of its form, the decolorizing composition may be applied to any liquid-permeable layer of the absorbent article where it can contact aqueous fluids exuded by the body (e.g., menses), such as the absorbent core 30, topsheet 26, intake layer 32, transfer delay layer (not shown), and so forth (See FIG. 1). The decolorizing composition may be applied continuously or discontinuously over some or all of a surface of a liquid-permeable layer (e.g., absorbent core, intake layer, transfer layer, etc.). In one embodiment, the decolorizing composition may cover only a portion of the surface to ensure that the layer is still capable of retaining sufficient absorbent properties. For example, the decolorizing composition may be present within the first peripheral zone 52, second peripheral zone 54, third peripheral zone 72 and/or fourth peripheral zone 74 of the absorbent article 20 of FIG. 1. In certain embodiments, it may be desired that the decolorizing composition is positioned closer to the absorbent core 30 to minimize potential leakage. Thus, in addition to or in lieu of the peripheral zones, the decolorizing composition may also be positioned within the first transition zone 62 and/or the second transition zone 64. This may be accomplished by applying the composition to a body-facing surface of the absorbent core 30 within the desired zones. Typically, however, it is desired that the interior zone 80 is left substantially untreated with the decolorizing composition so that a user is able to monitor the bodily exudates for infection or other health-related conditions.

In addition to being applied to the absorbent core 30, other configurations may also be employed in the present invention. For example, an additional layer (not shown) may be applied with the decolorizing composition that is in contact with the absorbent core 30. The additional layer may be formed from a variety of different porous materials, such as a perforated film, nonwoven web (e.g., cellulosic web, spunbond web, meltblown web, etc.), foams, etc. In one embodiment, the additional layer may be in the form of a hollow enclosure (e.g., sachet, bag, etc.) that is folded so that it partially or completely surrounds the absorbent core 30. The decolorizing composition may be disposed within this enclosure so that it remains sealed therein prior to use. In another embodiment, however, the additional layer may be the intake layer 32. Typically, the decolorizing composition is disposed on a surface facing away from the absorbent core 30; however, it should also be understood that the decolorizing composition may be positioned on any other surface, such as between the additional layer and the absorbent core 30.

Regardless of the particular embodiment employed, the printed patterns of the present invention are distributed in an asymmetric manner about both the longitudinal and transverse centerlines of the article, and are located at or near the periphery of the article and at least partially extend into portions of the body facing surface that overlie the absorbent core. Such a carefully selected layout and design helps visually mask the presence of bodily fluids or stains around the periphery of the article. The pattern design is also such that a majority of an interior zone of the absorbent article is generally free of printed graphical objects, which helps the user to better detect the presence of bodily fluids during use and further enhances the overall distinctive nature of the patterns. The absorbent article may also contain an "active" masking component (e.g., decolorizing combination) in combination with the unique patterns to provide a synergistic impact on the users overall experience with the product.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A feminine care absorbent article that defines a longitudinal centerline and a transverse centerline, wherein the article comprises:

a topsheet;

a baffle;

an absorbent core disposed between the topsheet and the baffle that defines a circumferential edge, wherein the topsheet and baffle extend outwardly from the circumferential edge and into a longitudinally extending first peripheral zone located on one side of the longitudinal centerline, a longitudinally extending second peripheral zone located along another side of the longitudinal centerline, a laterally extending third peripheral zone located on one side of the transverse centerline and between respective inboard dimensions of the first peripheral zone and the second peripheral zone, and a laterally extending fourth peripheral zone located on another side of the transverse centerline and between respective inboard dimensions of the first peripheral zone and the second peripheral zone, wherein a first transition zone extends circumferentially about an interior zone adjacent to the third peripheral zone and a second transition zone extends circumferentially about the interior zone adjacent to the fourth peripheral zone;

a passive masking component that includes a first printed pattern of discrete graphical objects located within the first peripheral zone and extending at least partially into the first transition zone, the second transition zone, or both, and a second printed pattern of discrete graphical objects located within the second peripheral zone and extending at least partially into the first transition zone, the second transition zone, or both, wherein the first printed pattern is asymmetrical with respect to the second printed pattern about both the longitudinal and transverse centerlines, wherein the first printed pattern and the second printed pattern are visible from a body facing surface of the topsheet, wherein the passive masking component does not change during use of the feminine care absorbent article, and further wherein a majority of the interior zone is free of printed graphical objects; and an active masking component located within the first peripheral zone, the second peripheral zone, the first transition zone, the second transition zone, or a combination thereof, wherein the active masking component directs the bodily fluid to a hidden location in the absorbent article, wherein the active maskinq component comprises a nonwoven web having a basis weight of from about 0.5 ounces per square yard to about 1 ounce per square yard, a nonwoven web adsorbed with an amphiphilic protein to define a gradient distribution along at least one dimension, or a fibrous web having a first zone of fibers treated with a surfactant and a second zone of fibers exposed to a corona field, and further wherein the interior zone is generally free of the active masking component.

2. The feminine care absorbent article of claim 1, wherein the first printed pattern, second printed pattern, or both are located on a body facing surface of the baffle.

3. The feminine care absorbent article of claim 1, wherein the first printed pattern, second printed pattern, or both are located on a body facing surface of the topsheet.

4. The feminine care absorbent article of claim 1, wherein the first printed pattern extends at least partially into the first transition zone and the second transition zone.

5. The feminine care absorbent article of claim 1, wherein the second printed pattern extends at least partially into the first transition zone and the second transition zone.

6. The feminine care absorbent article of claim 1, wherein a third printed pattern of discrete graphical objects is located within the third peripheral zone and a fourth printed pattern of discrete graphical objects is located within the fourth peripheral zone, wherein the third printed pattern is asymmetrical with respect to the fourth printed pattern about both the longitudinal and transverse centerlines, and wherein the third printed pattern and the fourth printed pattern are visible from a body facing surface of the topsheet.

7. The feminine care absorbent article of claim 6, wherein the third printed pattern extends at least partially into the first transition zone.

8. The feminine care absorbent article of claim 6, wherein the fourth printed pattern extends at least partially into the second transition zone.

9. The feminine care absorbent article of claim 1, wherein the third peripheral zone, the fourth peripheral zone, or both, are free of printed graphical objects.

10. The feminine care absorbent article of claim 1, further comprising laterally extending wings on which the first and second printed patterns, respectively, are at least partially located.

11. The feminine care absorbent article of claim 1, wherein the first and second peripheral zones have laterally outboard dimensions generally coextensive with at least a portion of the periphery of the absorbent article.

12. The feminine care absorbent article of claim 1, wherein the interior zone is free of printed graphical objects.

13. The feminine care absorbent article of claim 1, wherein the absorbent core contains embossed channels within the interior zone.

14. The feminine care absorbent article of claim 1, wherein the first and second printed patterns of discrete graphical objects convey a functional cue to a consumer.

15. The feminine care absorbent article of claim 1, wherein the discrete graphical objects of the first printed pattern have a shape, size, and/or color different than the discrete graphical objects of the second printed pattern.

16. The feminine care absorbent article of claim 1, wherein at least a portion of the topsheet is formed from a nonwoven web having a basis weight of from about 0.5 to 1 ounce per square yard and a denier of from about 4 to about 12.

17. The feminine care absorbent article of claim 1, wherein the article is a sanitary napkin.

* * * * *